(12) United States Patent
Nemana et al.

(10) Patent No.: US 7,618,822 B2
(45) Date of Patent: Nov. 17, 2009

(54) PREDICTIVE CRUDE OIL COMPATIBILITY MODEL

(75) Inventors: Sailendra Nemana, Carmichael, CA (US); Michael R. Kimbrell, Huntington Beach, CA (US); Eugene Zaluzec, Garden Grove, CA (US)

(73) Assignee: BP Corporation North America Inc., Warrenville, IL (US)

( * ) Notice: Subject to any disclaimer, the term of this patent is extended or adjusted under 35 U.S.C. 154(b) by 870 days.

(21) Appl. No.: 10/326,792

(22) Filed: Dec. 19, 2002

(65) Prior Publication Data

US 2004/0121472 A1   Jun. 24, 2004

(51) Int. Cl.
*G01N 33/24* (2006.01)
(52) U.S. Cl. .......................... 436/29; 436/25; 436/139; 436/179
(58) Field of Classification Search .................. None
See application file for complete search history.

(56) References Cited

U.S. PATENT DOCUMENTS

| | | | |
|---|---|---|---|
| 3,779,902 A | 12/1973 | Mitchell et al. | 208/251 |
| 4,264,429 A | 4/1981 | Rosenthal et al. | 208/10 |
| 4,671,103 A | 6/1987 | Dickakian | 73/61.1 |
| 4,762,797 A | 8/1988 | Dickakian | 436/60 |
| 4,853,337 A | 8/1989 | Dickakian | 436/55 |
| 5,871,634 A | 2/1999 | Wiehe et al. | 208/48 R |
| 5,997,723 A | 12/1999 | Wiehe et al. | 208/48 R |

OTHER PUBLICATIONS

Lin "The relationship between the characterization factor "K" and the solubility parameter "δ" of petroleum solvents", Proceedings of the National Science Council, Republic of China (1978), 2(3), 314-21.*
The Oil Compatability Model And Crude Oil Incompatability, Erwin A. Wiehe, Corporate Research Laboratories, Exxon Research and Engineering Company.

(Continued)

*Primary Examiner*—Yelena G Gakh
(74) *Attorney, Agent, or Firm*—Ekkehard Schoettle

(57) ABSTRACT

A method for blending at least two hydrocarbon liquids, the method comprising: (a) determining the critical solvent power for each hydrocarbon liquid by (i) mixing each hydrocarbon liquid with predetermined amounts of a paraffin; (ii) centrifuging each resulting mixture; (iii) recovering and weighing any resulting precipitated insolubles from step (ii); and (iv) correlating the weight of the insolubles in step (iii) to the solvent power at which asphaltenes begin to precipitate out of the hydrocarbon; (b) determining the solvent power for each hydrocarbon liquid by: (i) determining the distillation curve and density of each hydrocarbon liquid; (ii) numerically integrating the distillation curve of each hydrocarbon liquid, producing the volume average boiling point for each hydrocarbon liquid; (iii) calculating the characterization K factor for each hydrocarbon liquid using the volume average boiling point in step (ii); and (iv) determining the solvent power of each hydrocarbon liquid using the characterization K factor in step (iii), wherein heptane and toluene are used as solvent power references wherein heptane has a solvent power of zero and toluene has a solvent power of 100; and (c) blending the each crude oil into each other producing a crude oil blend wherein the solvent power of the crude oil blend is greater than the critical solvent power of the crude oil having the highest critical solvent power in the blend.

6 Claims, 2 Drawing Sheets

OTHER PUBLICATIONS

Mitigation of the Plugging of a Hydrotreater with the Oil Compatibility Model, Erwin A. Wiehe, Corporate Research Laboratories, Exxon Research and Engineering Company.

Prevention of Fouling by Incompatible Crudes with the Oil Compatibility Model, Erwin A. Wiehe, Corporate Research Laboratories, Exxon Research and Engineering Company.

* cited by examiner

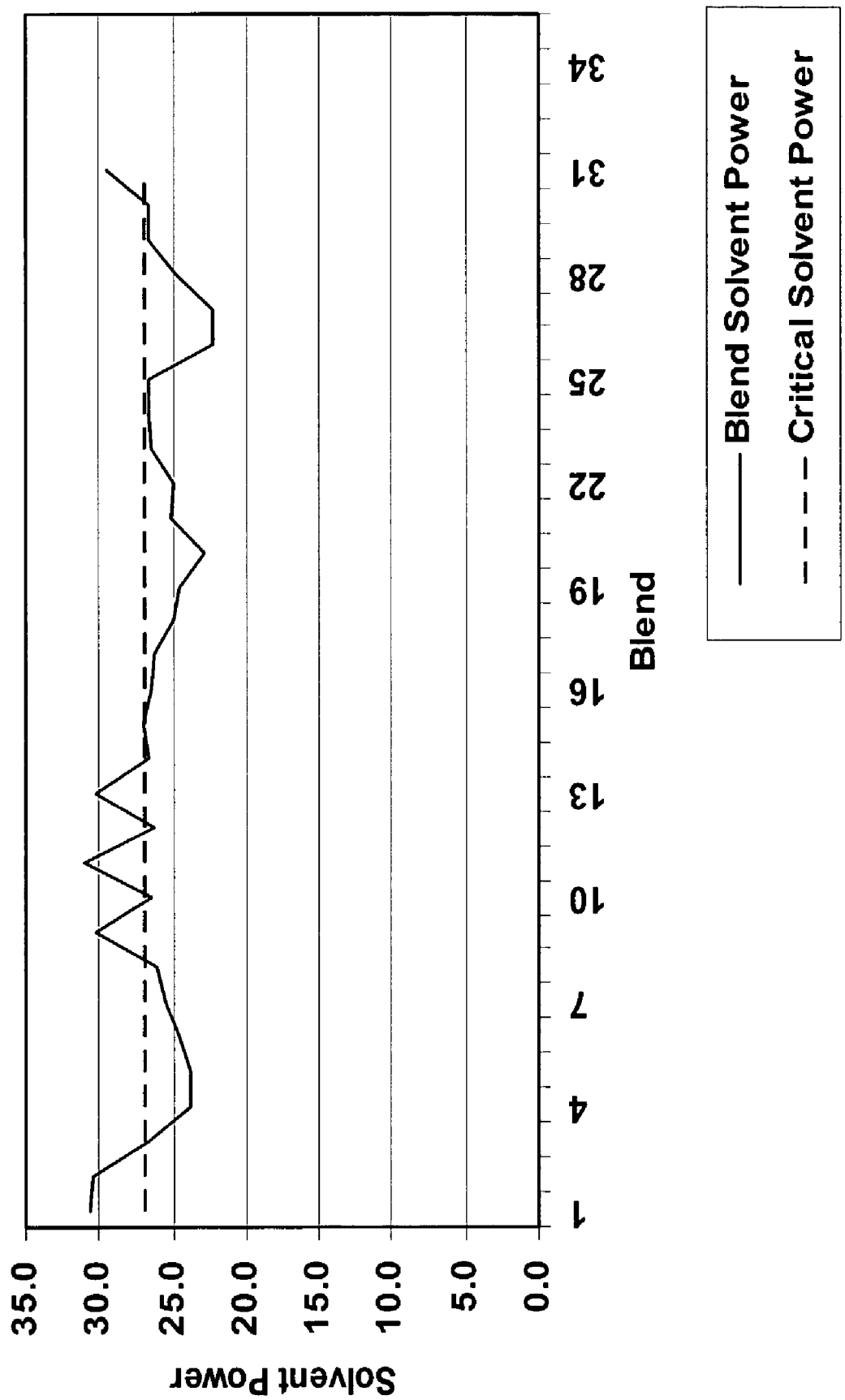

PREDICTIVE CRUDE OIL COMPATIBILITY MODEL

FIELD OF THE INVENTION

The present invention relates to a method for predicting the compatibility or incompatibility of blending two or more hydrocarbon liquids or crude oils together.

BACKGROUND OF THE INVENTION

In order to satisfy favorable economics for the refining of crude oil, it is often necessary to blend two or more crude oils prior to carrying out the various refining processes. However, there are particular problems associated with blending crude oils. One major problem is that crude oils are often incompatible with each other resulting in equipment fouling and ultimately equipment shutdown. Such equipment includes, but is not limited to, pipes, tanks, heat exchangers, furnaces, fractionators and reactors. Another major problem with blending crude oils and other hydrocarbons is the production of oil and water emulsions in the crude oil slop system preventing the oil slop from being processed by refinery equipment, such as crude distillation units. Another major problem is the production of emulsions in crude desalter units often having a deleterious effect upon the waste water system associated with the desalter unit. In light of these problems, crude oil incompatibility has been plaguing the refining industry for many years resulting in lost profits due to unnecessary equipment shutdown and limitations on the crude oil slate available for refining.

The primary culprit that causes incompatibility of crude oils is the presence of organic solids in the form of precipitated asphaltenes in blended crude oils. Current theory regarding the asphaltene-crude oil relationship postulates that such relationship is similar to a solute-solvent interaction wherein a certain solvent strength is required to hold asphaltenes in solution in crude oil. The primary parameter governing the ability of asphaltenes to remain in solution in crude oil is the aromatics to saturates ratio of the crude oil. It is known that asphaltenes are soluble in aromatics such as toluene, but insoluble in paraffinic compounds such as n-heptane. Accordingly, asphaltenes are defined herein as the non-volatile and polar fraction of crude oil that is insoluble in n-alkanes.

The underlying problem associated with the presence of asphaltenes in crude oils is that asphaltenes frequently precipitate from solution during the blending of two or more incompatible crude oils. This is generally thought to be caused by perturbations of the indigenous crude oil composition disrupting the delicate balance that keeps the asphaltenes soluble in crude oil. It is also believed that oil-water emulsions are formed and stabilized in part by the presence of precipitated asphaltenes from incompatible crude blends. Consequently, when left unchecked, asphaltene precipitation manifests itself in a variety of undesirable areas, including refinery equipment through the formation of coke and the generation of oil-water emulsions in storage tanks.

In the past, crude oil compatibility could be determined through extensive laboratory testing. For blends of two crude oils, the determination of crude oil compatibility is relatively straightforward since the number of tests required to define the acceptable blend ratios is relatively small. However, for each additional different stock of crude oil added to a blend, the number of lab tests required to ascertain the range of incompatibility goes up exponentially making the determination of crude oil compatibility intractable. This presents a difficulty when economic conditions justify blending three or more crude oils together for feed to crude distillation units or other refining processes. Accordingly, there is a need for a practical and cost efficient means for determining the viability of blending different crude oils.

In response to this need, the petroleum refining industry has devoted extensive resources and effort to develop new methods to solve the problem of blending different crude oils. However, such efforts have only partially succeeded in providing a practical yet cost effective method for blending different crude oils.

One such effort is U.S. Pat. No. 4,843,337 issued to Dickakian et al., which discloses a method for blending hydrocarbon liquids at a ratio to maintain the combined aromatic to asphaltene ratio above a certain predetermined level to prevent fouling of process equipment. However, the Dickakian disclosure is limited to a method for blending two hydrocarbon liquids leaving unsettled the problem of blending three or more crude oils.

U.S. Pat. No. 5,871,634 and U.S. Pat. No. 5,997,723, both issued to Wiehe et al., disclose a method for blending potentially incompatible crude oils by combining each crude oil in order of solubility blending numbers such that the solubility blending number of the mixture is greater than the insolubility number of any crude oil of the mixture. However, the Wiehe disclosures teaches a method that employs inexact and onerous laboratory tests, such as conventional optical microscopy or crude oil filtration to determine the presence of asphaltenes in each crude oil. Moreover, the Wiehe disclosure employs a complex blending and titration analysis to determine the insolubility number and the solubility blending number for each crude oil.

Although the foregoing disclosures provide advances in the art, there is still a need for a method for accurately determining crude oil incompatibility that is practical and cost efficient.

It has also been found that centrifuging one or more crude oils blended with predetermined amounts of heptane provides for a simple yet cost effective means for determining asphaltene instability and the amount of asphaltenes in each crude oil.

It has also been found that the relative ratio of aromatics to saturates in each crude oil to be blended can be easily determined by using the relationship between the boiling point and the density of each crude oil.

It has also been found that compatible blends of two or more crude oils can be determined based on the relationship between the boiling point and the density of each crude oil in the blend and the determination of asphaltene instability in each crude oil in the blend.

SUMMARY OF THE INVENTION

The present invention is directed to a method for blending at least two hydrocarbon liquids together by determining the critical solvent power for each hydrocarbon liquid, determining the solvent power for each hydrocarbon liquid, and thereafter blending the hydrocarbon liquids together, producing a hydrocarbon liquid blend having a solvent power that is greater than the critical solvent power of the hydrocarbon liquid having the highest critical solvent power in the blend.

As used herein, crude oil is understood to mean liquid petroleum and all other hydrocarbons, regardless of gravity, produced at a well in liquid form by ordinary production methods.

As used herein, a hydrocarbon liquid is understood to mean a fluid compound comprising hydrogen and carbon.

As used herein, solvent power is understood to mean the relative ratio of aromatics to saturates in a crude oil or a blend of crude oils.

As used herein, critical solvent power is understood to mean the solvent power at which asphaltenes begin to precipitate out of a crude oil or blend of crude oils.

The present invention also includes a method for determining the critical solvent power of one or more hydrocarbon liquids. The method includes the steps of mixing each hydrocarbon liquid with predetermined amounts of a normal paraffin, centrifuging each resulting mixture recovering and weighing any resulting precipitated insolubles from the mixture, and thereafter correlating the weight of the insolubles to a solvent power at which asphaltenes begin to precipitate out of the mixture.

The present invention also includes a method for determining the solvent power of one or more hydrocarbon liquids. The method includes the steps of determining the distillation curve and density of each hydrocarbon, numerically integrating the distillation curve of each hydrocarbon liquid, producing the volume average boiling point for each hydrocarbon liquid, calculating the modified characterization K factor for each hydrocarbon liquid using the volume average boiling point, and thereafter determining the solvent power of each hydrocarbon liquid using the calculated modified characterization K factor wherein heptane and toluene are used as solvent power references wherein heptane has a solvent power of zero and toluene has a solvent power of 100.

The present invention provides for a practical yet cost effective process for determining the solvent power of one or more hydrocarbon liquids and/or crude oils that does not require the complex blending and titration analysis to determine the insolubility number and the solubility blending number for each hydrocarbon liquids and/or crude oils.

The present invention also provides for a practical yet cost effective process for determining the amount of asphaltenes in one or more hydrocarbon liquids and/or crude oils allowing for the determination of the optimal blend of two or more hydrocarbon liquids and/or crude oils during a variety of economic conditions.

The present invention also provides for a practical yet cost effective process for determining the compatibility of two or more crude oils together facilitating the flexibility of choosing a wide variety of crude oil slates for processing in a crude oil refinery The present invention also provides a practical yet cost effective process for blending two or more hydrocarbon liquids and/or crude oils for processing in a refinery without the threat of asphaltene precipitation reducing unit downtime due to fouling or coke formation of lines or in equipment caused by incompatible blends of crude oil.

The present invention also provides for energy savings by preventing heat exchanger fouling caused by blending incompatible hydrocarbon liquids and/or crude oils.

The present invention also provides for a method of eliminating crude oil from desalter unit's effluent water preventing upsets in the waste water system and wastewater discharge. Similarly, water carry over with the oil from the desalter will be eliminated, minimizing unstable operation of the crude distillation unit.

Although the subject invention is presented herein primarily as it applies to crude oils, it is understood to one of ordinary skill in the art that the subject invention may also be applicable with other hydrocarbon liquids where precipitation of insolubles and fouling are of concern.

BRIEF DESCRIPTION OF THE DRAWINGS

FIG. 2 depicts fouling level risks of a refinery process unit resulting from the blending of multiple crude oils over a period of time.

DESCRIPTION OF THE PREFERRED EMBODIMENT(S)

Figure 1:
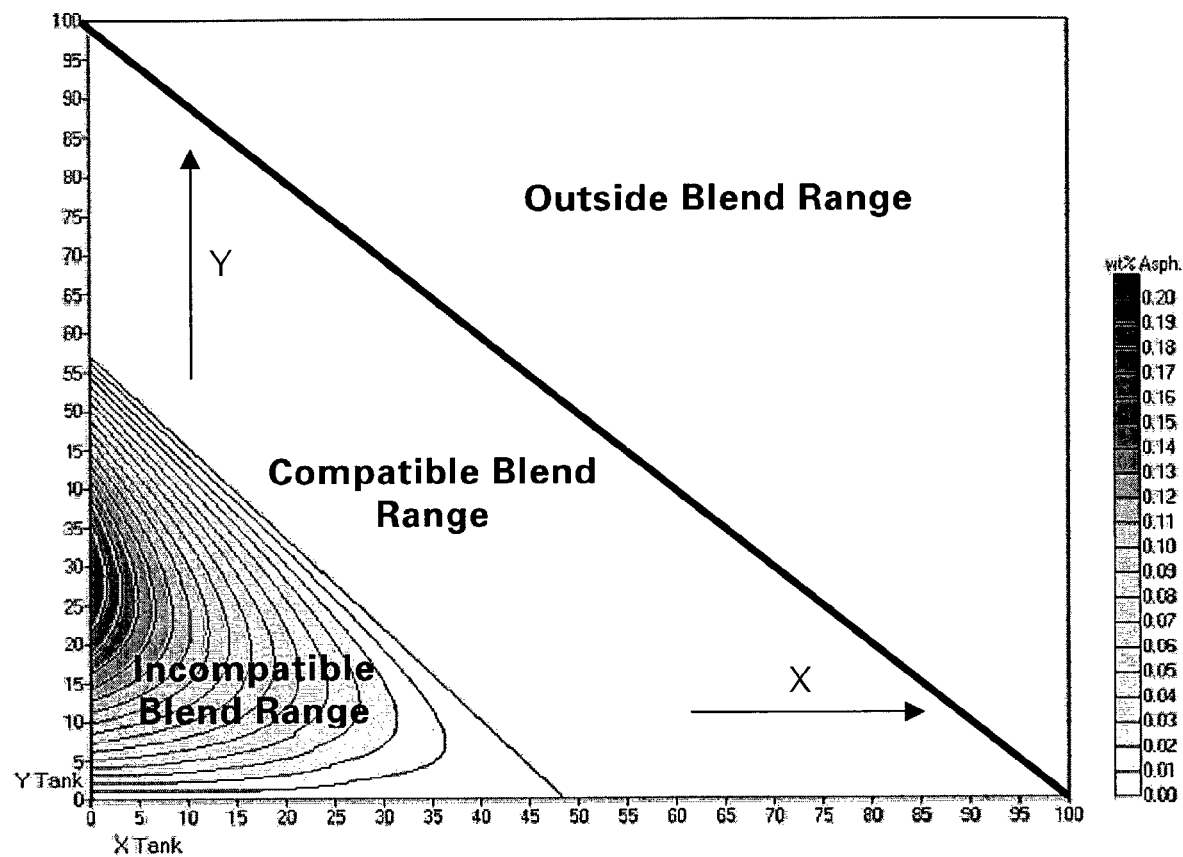
FIG. 1 depicts an embodiment of a process in accordance with the present invention graphically illustrating continuous predictive modeling for blending three different crude oils together.

In greater detail, the subject invention is directed to a method for blending two or more crude oils together in a manner to prevent asphaltene precipitation from the crude oil blend. More particularly, the subject invention comprises a method for determining the solvent power and critical solvent power of the crude oils that are candidates for blending, and thereafter blending the crude oils together such that the solvent power of the blended crude oils is greater than the critical solvent power of the crude oil having the greatest critical solvent power in the blend. As previously stated, solvent power is understood to mean the relative ratio of aromatics to saturates in a crude oil or a blend of crude oils and critical solvent power is understood to mean the solvent power at which asphaltenes begin to precipitate out of a crude oil or a crude oil blend.

Each crude oil has a unique solvent power and unique critical solvent power. If two or more crude oils are blended together, the solvent power of the resulting blend varies between the solvent powers of each crude oil in the blend. Considering this, it is of paramount concern to accurately and precisely predict the solvent power of a crude oil blend in order maintain asphaltenes in the crude oil blend in a soluble state. To address this paramount concern, the subject invention includes: (1) a method for determining the solvent power of one or more crude oils; (2) a method for determining the critical solvent power of one or more crude oils, and (3) a method for blending two or more crude oils together.

Determining Crude Oil Solvent Power

As previously stated, past practice used repetitive lab testing to determine a crude oil's solvent power. Considering, however, that the primary parameter governing the ability of asphaltenes to remain in solution in crude oil is the aromatics to saturates ratio of the crude oil, it is possible to accurately model crude oil as a solvent using assay data, including distillation data and density data, of the crude oil. By using the relationship between the distillation data and the density data of a crude oil, the relative ratio of aromatics to saturates in the crude oil can be determined. Therefore, the solvent power of one or more crude oils can be determined as more particularly described herein.

In determining the solvent power of a particular crude oil, it is preferred to obtain assay data for the selected crude oil. The preferred assay data are distillation data and density data of the selected crude oil. If such data is not readily available or it is suspected that available assay data is inaccurate, a conventional high temperature simulated distillation can be easily conducted to provide the preferred distillation data of a particular crude. The density of the crude oil can be obtained by any conventional method known to those skilled in the art.

Typical distillation simulations used in the refining industry are ASTM and true boiling point (TBP) analytical distillations, which are often both used to define the volatility characteristics of petroleum fractions and other complex mixtures. Both are batch distillations, which differ mainly in the degree of fractionation obtained in the distillation. ASTM distillations are more convenient than TBP distillations because ASTM distillations are simpler, less expensive, require less sample, and require only approximately one-tenth as much time. The ASTM distillations methods used today include: ASTM Method D86; ASTM Method D1160; ASTM Method D2887; ASTM Method D2892; and ASTM Method D3710. As is appreciated by those skilled in the art, the method of distillation employed often depends upon the petroleum fraction that is to be distilled.

Although the distillation data from any of these distillation methods is suitable for the subject invention, it is preferred that the distillation data derive from an ASTM Method D86 distillation. If the available distillation data for the present invention is not from an ASTM Method D86 distillation, the distillation data is preferably converted to a D86 distillation curve. This conversion can be done manually according to the API method of conversion as disclosed in *API Technical Data Book, Chapter 3: Petroleum Fraction Distillation Interconversions*, 5$^{th}$ ed., 1992, which is incorporated herein by reference. However, it is preferred to conduct the conversion using HYSYS, PRO II, or any other computer program that uses the API method of conversion. If HYSYS or PRO II is used for the conversion, it is preferred that a probability method of curve extrapolation is used.

The next step in determining the solvent power of a particular crude is to numerically integrate the distillation curve, preferably a D86 distillation curve, from 0% to 100% and divide by 100. This integration gives the volume average boiling point (VABP) of the selected crude oil and is given by:

$$VABP = \int_0^{100} \frac{T(X)dx}{100}$$

In integrating the distillation curve, the preferred method is to fit the distillation curve to a cubic spline function (third order polynomial function), which is then integrated numerically at 1% increments.

Once the distillation curve is integrated, it is preferred to calculate the characterization factor K of the selected crude oil, $K_{oil}$, using the volume average boiling point and the density of the selected crude oil. The characterization factor K is based on Watson K factor as described in *API Technical Data Book, Chapter 2: Petroleum Fraction Distillation Interconversions*, 5$^{th}$ ed., 1992, which is incorporated herein by reference. Preferably, the calculation to determine the characterization factor K is given by:

$$K_{oil} = \frac{(VABP)^{\frac{1}{3}}}{SG}, \text{ wherein } SG \text{ is the specific gravity of oil}$$

Once the characterization factor K of the selected crude oil is calculated, the solvent power of the selected crude is easily determined. The solvent power of the selected crude oil is preferably defined using heptane and toluene as references, wherein heptane has a solvent power of zero and toluene has a solvent power of one hundred. Thus, a crude oil with solvent power of zero is equivalent to heptane, and a crude oil with a solvent power of one hundred is equivalent to toluene. Typically, most crude oils do not have a solvent power greater than fifty, which is about cyclohexane equivalent. Preferably, the determination of the solvent power of a crude oil is given by:

$$SP = \left[ \frac{K_{oil} - 12.79}{10.196 - 12.79} \right] \times 100$$

Thus:
when SP=0, oil is approximately heptane equivalent;
when SP=100, oil is approximately toluene equivalent;
when SP=50, oil is approximately cyclohexane equivalent.

As one of ordinary skill in the art would appreciate, determining the solvent power of one or more crude oils or hydrocarbon liquids, as described herein, is relatively simplistic and provides a useful tool in determining the compatibility of blending a plurality of crude oils. Another useful yet simplistic tool in determining the compatibility of blending a plurality of crude oils is the determination of the critical solvent power of one or more crude oils as described herein.

Determining the Critical Solvent Power

Experimental evidence shows that below a certain threshold solvent power, asphaltenes precipitate out of crude oil. This threshold is called the critical solvent power of the crude oil. At solvent powers above the critical value, asphaltenes stay in solution and precipitation is prevented. Considering that the solvent power of crude oil is the relative ratio of saturates to aromatics, the determination of the critical solvent power as contemplated herein employs a simplistic paraffin (saturate) titration with each crude oil that is a candidate for blending.

In accordance with the present invention, it is preferred that a paraffin is incrementally added to a crude oil that is a candidate for blending with one or more different crude oils. It is preferred that the paraffin is normal heptane (n-heptane). However, other paraffins, such as normal pentane or iso-octane, may be suitable for the present invention. As the concentration of the paraffin increases in the crude oil, the ratio of saturates to aromatics increases until asphaltenes begin to precipitate out of the crude oil. The point of initial asphaltene precipitation represents the critical solvent power of the crude oil. The critical solvent power of the tested crude oil is documented for future determinations of its blending compatibility with other crude oils.

In a preferred embodiment, at least about a 50 ml. sample of the selected crude oil is obtained to determine its critical solvent power. Predetermined amounts of a suitable paraffin is incrementally added to the crude oil sample, mixed and allowed to equilibrate. It is preferred that n-heptane is incrementally added to the crude oil sample in at least about 1:5 ratio as measured in wt. %, vol. % or mol. %. It is more preferred that n-heptane is added to the crude oil sample in at least about 1:10 ratio as measured in wt. %, vol. % or mol. %. It is most preferred that n-heptane is added to the crude oil sample in at least about 1:20 ratio as measured in wt. %, vol. % or mol. % for best results.

From the selected sample, it is preferred to prepare separate solutions of the selected crude oil and n-heptane. The prepared solutions preferably have varying ratios of n-heptane to the selected crude oil. For example a 100 ml. sample of a selected crude may be separated into 10 sample tubes. One sample tube preferably contains 100 wt. % crude oil while the remaining nine sample tubes preferably contain a solution of the selected crude oil and varying amounts of n-heptane. The sample tubes preferably have solutions with increasing concentrations of n-heptane, preferably in 10% wt. % increments. For example, sample tube 1 contains 100 wt. % crude oil, sample tube 2 contains 90 wt. % crude oil and 10 wt. % n-heptane, and sample tube 3 contains 80 wt. % crude oil and 20 wt. % n-heptane, and so forth. A final sample tube preferably has 100 wt. % n-heptane.

The samples are thoroughly mixed and allowed to equilibrate and then centrifuged. The centrifuging process can be carried out by any conventional centrifuge available on the market, such as an Eppendorf Micro Centrifuge 5415C. The sample tubes are preferably centrifuged at least about 10,000 rpm, more preferably at least about 11,000 rpm, and most preferably at least about 12,000 rpm for at least about 10 mins, more preferably at least about 15 mins and most preferably at least about 20 mins.

After the samples have been centrifuged, the supernatant liquid is removed and the precipitate, if any is recovered. The precipitate represents asphaltenes insoluble in a particular sample tube. The asphaltenes are subsequently washed in a normal paraffin, preferably n-heptane or n-pentane. The recovered insolubles are then weighed in preferably wt. % and plotted against the weight % of n-heptane or n-pentane of the solution of the particular sample tube.

The critical solvent power is calculated at the point of the resulting plot where asphaltenes begin to precipitate. This is done by determining the solvent power of the solution of the sample tube where asphaltene precipitation began. The solvent power of the solution is calculated as indicated in the solvent power calculation procedure previously described. The difference in the distillation curve will be in the amount of heptane recovered at 98.5° C., the boiling point of heptane. The gravity of the crude oil will also become less with the addition of heptane.

In addition to determining the critical solvent power of a crude oil, the resulting plot results in a curve that describes the asphaltene equilibrium between the precipitated and soluble states of asphaltenes below the critical solvent power of the tested crude oil. This curve is advantageous because it is useful in predicting the total amount of asphaltenes in a crude oil and the amount of asphaltene precipitation at various solvent powers below the crude oil's critical solvent power.

Blending Two or More Crude Oils

If two or more crude oils are blended together, the blend solvent power varies between the solvent powers of each crude oil. Determining the solvent power for a two crude oil blend is relatively simple since it can be calculated analytically. However, as each additional crude oil is added to the blend, the degrees of freedom increase such that the number of potential blends goes up exponentially. For example, for five crude oils blended in 10% increments, the number of blends to be evaluated for compatibility is in the thousands. Consequently, it becomes increasingly difficult to analytically compute the solvent power and compatibility of the crude oil blend as the number of crude oils in the blend increases. For this reason, a Monte Carlo simulation is preferably used to select a representative number of different blends to calculate the solvent power at each blend ratio and compare to the critical solvent power of each crude oil, thereby creating enough representative data points to accurately model the blending compatibility of two or more crude oils.

The Monte Carlo simulation in its basic terms simply accounts for the probabilities of each potential outcome for a potential variable and uses a random number generator to assign a value to each variable. As used in the subject invention, the Monte Carlo simulation varies the fraction of each crude oil in a crude oil blend preferably to a weight fraction probability distribution function that the user provides. In a preferred embodiment, the Monte Carlo simulation technique chooses random crude oil blend ratios of selected crude oils. The weight fraction of asphaltenes, if any, precipitated in the random crude oil blends is then calculated at each of the randomly selected blend ratios.

When using the Monte Carlo technique, it is preferred to have a stipulation that the error in the crude oil blend solvent power calculation is not greater than a specified error. It is preferable that the error in the crude oil blend solvent power calculation is not greater than 0.5 SP (E=0.5). The number of iterations required is preferably on the order of $$\left(\frac{1}{E}\right)^{\frac{n}{r}}$$

where r is the smoothness of the asphaltene solubility curve and n is the number of crude oils in the blend. It is preferred that r=0.3. Thus, for 2 crude oils in the blend, 100 random points are generated. For 3 crude oils in the blend, 1000 random points are generated.

It is assumed that the solvent power of the crude oil blends linearly by weight. Saying this, the solvent power of the crude oil blend is equal to the sum of the product of the weight fraction of the crude oil in the blend to the solvent power of the crude oil, which is given by:

$$SP_{blend} = \sum_{i=1}^{n} X_i SP_i,$$

wherein
 $SP_{blend}$ is the solvent power of the blend;
 $X_i$ is the weight fraction of crude i in the blend;
 $SP_i$ is the solvent power of crude i; and
 n is the number of crude oil in the blend.

To prevent incompatibility, the blend solvent power should be greater than the critical solvent power of the crude oil having the highest critical solvent power in the blend. It is preferable that the blend ratio of the crude oils is at least about 15 vol. percent greater than the blend ratio at the critical solvent power of the crude oil having the highest critical solvent power in the blend. It is even more preferable that the blend ratio of the crude oils is at least about 10 vol. percent greater than the blend ratio at the critical solvent power of the crude oil having the highest critical solvent power in the blend. However, it is even most preferable that the blend ratio of the crude oils is at least about 5 vol. percent greater than the blend ratio at the critical solvent power of the crude oil having the highest critical solvent power in the blend. Alternatively, it is preferable that the solvent power of the crude oil blend is at least 15 percent greater than the critical solvent power of the crude oil having the highest critical solvent power in the crude oil blend. It is even more preferable that the solvent power of the crude oil blend is at least 10 percent greater than the critical solvent power of the crude oil having the highest critical solvent power in the crude oil blend. However, it is even most preferable that the solvent power of the crude oil blend is at least 5 percent greater than the critical solvent power of the crude oil having the highest critical solvent power in the crude oil blend.

Although the present invention has been described with particularity and detail, the following example provides further illustration of the invention and is understood not to limit the scope of the invention.

EXAMPLE #1

Example 1, which is graphically depicted in FIG. 1, represents a predictive model in accordance with the subject invention wherein crude oil X, crude oil Y and crude oil Z are blended in a three-component blend. As depicted in FIG. 1, the model ranges in % vol. where the separate crude oils are compatible and incompatible for blending. The X-axis represents % vol. of crude oil X and the Y-axis represents % vol. of crude oil Y. The balance at any point is the % vol. of crude oil Z. Crude oil X has a solvent power of 40.0 and critical solvent power of 27.2. Crude oil Y has a solvent power of 37.3 and a critical solvent power of 30.1. Crude oil Z has a solvent power of 22.2 and a critical solvent power of 16.6. In addition to predicting the incompatibility of crude oil blends, the "Incompatible Blend Range" range also illustrates the amount of aphaltenes in % wt. expected to precipitate out of the crude oil blend at that blending range.

EXAMPLE #2

Example 2 is a predictive model of process unit fouling (asphaltene precipitation) resulting from the blending of various crude oils at a refinery over a period of time. The model is graphically depicted in FIG. 2 and numerically depicted in the Table. FIG. 2 depicts the solvent power of the various blends in comparison with the critical solvent power of the crude oil having the highest critical solvent power in each blend. The solvent powers of each crude oil and each crude oil blend were calculated as described herein. The critical solvent powers of each crude oil were calculated as described herein. The Table numerically illustrates FIG. 2 at selected representative time periods. The Table also shows the solvent powers of each crude oil in the various blends and the weight % fraction each crude oil contributes to the various blends. The data from Example 2 predicts that where the blend solvent power is less than a critical solvent power of 26.9 significant fouling occurs in refinery process units.

TABLE

| Period 1 | | | Period 13 | | | Period 23 | | | Period 31 | | |
| --- | --- | --- | --- | --- | --- | --- | --- | --- | --- | --- | --- |
| Crude Oil | SP | Wt. % Fract. | Crude Oil | SP | Wt. Fract. | Crude Oil | SP | Wt. Fract. | Crude Oil | SP | Wt. Fract. |
| A1 | 29.7 | 3.7 | B1 | 31.0 | 14.8 | C1 | 27.8 | 29.1 | D1 | 27.8 | 11.6 |
| A2 | 21.0 | 3.9 | B2 | 22.1 | 11.5 | C2 | 22.1 | 9.4 | D2 | 22.1 | 16.2 |
| A3 | 32.4 | 26.6 | B3 | 32.4 | 9.0 | C3 | 32.4 | 5.5 | D3 | 32.4 | 2.6 |
| A4 | 28.8 | 6.8 | B4 | 28.8 | 3.0 | C4 | 29.9 | 4.4 | D4 | 26.8 | 13.0 |
| A5 | 26.4 | 2.0 | B5 | 29.9 | 23.0 | C5 | 39.4 | 3.5 | D5 | 16.4 | 6.5 |
| A6 | 39.4 | 24.1 | B6 | 26.4 | 2.0 | C6 | 28.6 | 16.4 | D6 | 19.7 | 15.5 |
| A7 | 28.6 | 8.8 | B7 | 39.4 | 16.0 | C7 | 19.7 | 11.0 | D7 | 26.1 | 12.7 |
| A8 | 19.7 | 13.5 | B8 | 28.6 | 12.0 | C8 | 26.1 | 5.3 | D8 | 22.2 | 7.6 |
| A9 | 35.0 | 4.1 | B9 | 19.7 | 2.7 | C9 | 22.2 | 7.4 | D9 | 23.3 | 14.3 |
| A10 | 22.2 | 2.9 | B10 | 26.1 | 3.1 | C10 | 23.3 | 8.0 | | | |
| A11 | 23.3 | 3.6 | B11 | 23.2 | 2.9 | | | | | | |
| Blend SP: 30.6 | | | Blend SP: 30.3 | | | Blend SP: 26.4 | | | Blend SP: 24.4 | | |
| Crit. SP: 26.9 | | | Crit. SP: 26.9 | | | Crit. SP: 26.9 | | | Crit. SP: 26.9 | | |

That which is claimed is:

1. A crude oil blend comprising two or more crude oils blended by a method comprising the steps of:
   (a) determining the critical solvent power for each crude oil by:
      (i) mixing each crude oil with predetermined amounts of a paraffinic hydrocarbon having a solvent power of zero;
      (ii) centrifuging each resulting mixture;
      (iii) recovering and weighing any resulting precipitated asphaltenes from step (ii); and
      (iv) correlating the weight of the precipitated asphaltenes in step (iii) to the solvent power at which asphaltenes begin to precipitate out of the crude oil;
   (b) determining the solvent power for each crude oil by:
      (i) determining the distillation curve and density of each crude oil;
      (ii) numerically integrating the distillation curve of each crude oil producing the volume average boiling point for each crude oil;
      (iii) calculating the characterization K factor for each crude oil using the volume average boiling point in step (ii); and
      (iv) determining the solvent power of each crude oil using the characterization K factor in step (iii); and
   (c) blending each crude oil into each other producing a crude oil blend wherein the solvent power of the crude oil blend is greater than the critical solvent power of the crude oil having the highest critical solvent power in the blend;
   wherein a Monte Carlo simulation is used to select a plurality of different blend ratios of the two or more crude oils to calculate the solvent power in step (b) of each crude oil blend.

2. The crude oil blend of claim 1, wherein the crude oil blend comprises three or more crude oils.

3. The crude oil blend of claim 1, wherein the crude oil blend comprises four or more crude oils.

4. The crude oil blend of claim 1, wherein the solvent power of the crude oil blend is at least 5 percent greater than the critical solvent power of the crude oil having the highest critical solvent power in the crude oil blend.

5. The crude oil blend of claim 1, wherein the solvent power of the crude oil blend is at least 10 percent greater than the critical solvent power of the crude oil having the highest critical solvent power in the crude oil blend.

6. The crude oil blend of claim 1, wherein the solvent power of the crude oil blend is at least 15 percent greater than the critical solvent power of the crude oil having the highest critical solvent power in the crude oil blend.

* * * * *